US012788617B2

(12) United States Patent
Luo

(10) Patent No.: US 12,788,617 B2
(45) Date of Patent: Nov. 10, 2026

(54) MANDIBULAR ADVANCEMENT DEVICE WITH AN ADJUSTMENT PART

(71) Applicant: DCSTAR INC, New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/777,086

(22) Filed: Jul. 18, 2024

(65) Prior Publication Data

US 2026/0020976 A1 Jan. 22, 2026

(51) Int. Cl.
*A61F 5/56* (2006.01)

(52) U.S. Cl.
CPC .................................... *A61F 5/566* (2013.01)

(58) Field of Classification Search
CPC ...... A61F 2005/563; A61F 5/56; A61F 5/566; A61C 7/08; A61C 7/36; A63B 71/085; A63B 2071/086; A63B 2071/088
See application file for complete search history.

(56) References Cited

U.S. PATENT DOCUMENTS 5,499,633 A * 3/1996 Fenton .................... A61F 5/566 128/859
5,666,974 A * 9/1997 Hiro ..................... A63B 71/085 128/862
5,876,199 A * 3/1999 Bergersen ................ A61C 7/08 433/6
8,833,374 B2 * 9/2014 Fallon ..................... A61F 5/566 433/68
2007/0292817 A1 * 12/2007 Schneider ............. F27D 1/1816 427/427
2007/0292819 A1 * 12/2007 Scarberry ........... B29C 33/3857 433/140
2019/0021901 A1 * 1/2019 LeBlanc .................. A61C 7/36
2021/0162156 A1 * 6/2021 Farrell .............. A61M 16/0493

* cited by examiner

*Primary Examiner* — Camtu T Nguyen
(74) *Attorney, Agent, or Firm* — Birch, Stewart, Kolasch & Birch, LLP

(57) ABSTRACT

A mandibular advancement device with an adjustment part, including an upper tray assembly, a lower tray assembly, and an adjustment part. The upper tray assembly includes an upper frame and an upper moldable component; the lower tray assembly includes a lower frame and a lower moldable component. At least two different materials are used in the manufacture of the upper tray assembly and/or the lower tray assembly. The adjustment part is configured to connect the upper tray assembly and the lower tray assembly by a snap-fit, as well as to adjust the position of the lower tray assembly relative to the upper tray assembly. Specifically, the snap-fit includes at least one protrusion on one side of the upper tray assembly and/or the lower tray assembly, and the protrusion is configured to compressively connect the upper frame and the lower frame.

20 Claims, 18 Drawing Sheets

MANDIBULAR ADVANCEMENT DEVICE WITH AN ADJUSTMENT PART

TECHNICAL FIELD

This disclosure pertains to a mandibular advancement device, specifically involving devices for use to prevent or reduce snoring and/or obstructive sleep apnea (OSA).

BACKGROUND

Snoring and sleep apnea are closely related to OSA, as snoring is often a common symptom or precursor of OSA. OSA is a sleep disorder characterized by pauses in breathing or periods of reduced breathing during sleep due to partial or complete blockage of the upper airway. This blockage is typically caused by the relaxation of soft tissues, collapse of the base of the tongue, and soft palate during sleep, leading to restricted airflow. Snoring is essentially caused by the vibration of obstructed airflow within the constricted space, creating characteristic noise. This obstruction can be partial or complete. When the airway is fully blocked, sleep apnea occurs, leading to temporary cessation of breathing, depriving the brain and body of oxygen, and disrupting the normal sleep cycle. Although snoring and sleep apnea might be seen as common phenomena, they warrant attention when their frequency increases or severity impacts sleep quality and health. In cases of OSA, such blockage can occur dozens or even hundreds of times per night, causing multiple breathing pauses and severely disrupting sleep. This not only results in excessive daytime sleepiness and decreased concentration but also increases the risk of chronic conditions such as cardiovascular diseases and diabetes.

The severity of OSA should not be underestimated, as it can have a broad and serious impact on an individual's health and life. OSA is a common yet often underestimated sleep disorder with severity levels ranging from mild to severe. One of the risks includes increased cardiovascular disease due to sustained airway obstruction leading to lower oxygen levels in the blood, causing elevated blood pressure and additional strain on the cardiovascular system. Additionally, OSA is closely associated with metabolic diseases like diabetes and obesity and may lead to decreased cognitive function, emotional and psychological health issues, and an increased risk of hazardous behaviors and accidents. Given the gravity of OSA, effective treatment becomes crucial.

Currently, there are multiple options for treating snoring, sleep apnea, or OSA. Continuous Positive Airway Pressure (CPAP) therapy is one of the most commonly used methods but comes with drawbacks such as inconvenience, adaptability issues, mask leaks, and sleep disturbances. Consequently, some individuals turn to oral appliances as an alternative. Among these, the Mandibular Advancement Device (MAD) is a common oral appliance that works by adjusting the position of the lower jaw relative to the upper jaw to increase airflow through the throat, thus improving sleep quality and reducing or eliminating symptoms of snoring and/or sleep apnea.

The primary limitation of mandibular advancement devices is that their fabrication process requires customization based on the user's dental or oral structure. Given the uniqueness of each individual's oral structure and dental alignment, customized models are designed to ensure that the mandibular advancement device fits well with the user's teeth and mouth, providing optimal effectiveness and comfort. However, this customization process generally requires assembly, molding, or adjustments by dental professionals and manufacturing labs, which is not only time-consuming and labor-intensive but also costly. With advancements in digital technology, alternative methods for customizing mandibular advancement devices have emerged, such as intra-oral scanning technology combined with Computer-Aided Design and Manufacturing (CAD/CAM) or 3D printing technologies. While these methods have reduced production times, they still involve dental professionals and manufacturing labs. Moreover, although these methods may reduce some costs, their overall expense remains high.

SUMMARY

The present disclosure provides a durable, easy-to-wear, and easy-to-use mandibular advancement device that adapts to the user's dental structure and reduces production costs. Furthermore, the disclosure aims to offer a comfortable solution that effectively alleviates symptoms of snoring and/or sleep apnea. Most importantly, the disclosure provides a straightforward mandibular advancement device that even non-technical users can easily utilize and wear, without relying on costly and time-consuming customization processes by dental professionals and manufacturing labs, thereby reducing the cost of usage.

A mandibular advancement device with an adjustment part is provided. The mandibular advancement device includes an upper tray assembly, a lower tray assembly, and an adjustment part. The upper tray assembly is generally arch-shaped to conform to the curvature of an upper dental arch of a user, and the lower tray assembly is generally arch-shaped to conform to the curvature of a lower dental arch of the user. The upper tray assembly includes an upper frame and an upper moldable component, while the lower tray assembly includes a lower frame and a lower moldable component. The upper tray assembly and/or the lower tray assembly include at least two different materials. The adjustment part is configured to connect the upper tray assembly and the lower tray assembly by a snap-fit and to adjust the position of the lower tray assembly relative to the upper tray assembly. The snap-fit includes at least one protrusion on one side of the upper tray assembly and/or the lower tray assembly, and the protrusion is configured to compressively connect the upper frame and the lower frame.

In one embodiment, the upper tray assembly is configured to contact the upper dental arch of the user.

In one embodiment, the lower tray assembly is configured to contact the lower dental arch of the user.

In one embodiment, the upper moldable component is configured to soften upon heating to allow it to be adjusted and molded into a shape to match the upper dental arch when the user bites down.

In one embodiment, the lower moldable component is configured to soften upon heating to allow it to be adjusted and molded into a shape to match the lower dental arch when the user bites down.

In another embodiment, a mandibular advancement device with an adjustment part is provided. The mandibular advancement device includes an upper tray assembly, a lower tray assembly, and an adjustment part. The upper tray assembly includes an upper frame and an upper moldable component, while the lower tray assembly includes a lower frame and a lower moldable component. The upper tray assembly and/or the lower tray assembly includes at least two different materials. The adjustment part is configured to connect the upper tray assembly and the lower tray assembly by a snap-fit and to adjust the position of the lower tray assembly relative to the upper tray assembly. The snap-fit includes at least one protrusion on one side of the upper tray assembly and/or the lower tray assembly, and the protrusion is configured to compressively connect the upper frame and the lower frame. The upper frame and the lower frame each have at least one inner wall and at least one outer wall, with a distance between the at least one inner wall and the at least one outer wall at least partially between 0.3 mm and 8 mm.

In one embodiment, the at least one protrusion is provided on a surface of the at least one outer wall of the upper frame, and at least one protrusion receiving part is provided on a surface of the at least one outer wall of the lower frame, and is opposite the at least one protrusion.

In one embodiment, the at least one protrusion is provided on the surface of the at least one outer wall of the lower frame, and at least one protrusion receiving part is provided on the surface of the at least one outer wall of the upper frame, and is opposite the at least one protrusion.

In one embodiment, the upper moldable component and the lower moldable component include a flexible thermoplastic material.

In one embodiment, the upper frame and the lower frame at least partially include a relatively rigid material compared to the upper moldable component and lower moldable component.

In yet another embodiment, a mandibular advancement device with an adjustment part is provided. The mandibular advancement device includes an upper tray assembly, a lower tray assembly, and an adjustment part. The upper tray assembly includes an upper frame and an upper moldable component, while the lower tray assembly includes a lower frame and a lower moldable component. The upper tray assembly and/or the lower tray assembly includes at least two different materials. The adjustment part is configured to connect the upper tray assembly and the lower tray assembly by a snap-fit and to adjust the position of the lower tray assembly relative to the upper tray assembly. The upper frame and the lower frame each have at least one inner wall, with an angle formed between the at least one inner wall and a horizontal plane between 20° to 150°.

In one embodiment, the total weight of the upper frame and the lower frame is between 3 g to 50 g.

In one embodiment, the total weight of the mandibular advancement device is between 8 g to 80 g.

In one embodiment, the snap-fit of the adjustment part is configured in one of the following shapes: I-shaped, F-shaped, E-shaped, or symmetrically E-shaped.

In one embodiment, the adjustment part is configured to adjust multiple positions.

In another embodiment, a mandibular advancement device with an adjustment part is provided. The mandibular advancement device includes an upper tray assembly, a lower tray assembly, and an adjustment part. The upper tray assembly includes an upper frame and an upper moldable component, while the lower tray assembly includes a lower frame and a lower moldable component. The upper tray assembly and/or the lower tray assembly include at least two different materials. The adjustment part is configured to connect the upper tray assembly and the lower tray assembly by a snap-fit and to adjust the position of the lower tray assembly relative to the upper tray assembly. The upper frame and the lower frame each have at least one inner wall, at least one outer wall, and at least one bottom wall. And the upper frame and the lower frame have one or more of the following characteristics: a. a vertical distance between the at least one inner wall, the at least one outer wall, and the at least one bottom wall between 0.5 mm to 20 mm; b. a total circumference of the at least one outer wall between 2 mm to 200 mm; and c. a total area of the at least one outer wall between 50 $mm^2$ to 2000 $mm^2$.

In one embodiment, the thickness of the at least one bottom wall of the upper frame and the lower frame is between 0.5 mm to 20 mm.

In one embodiment, the upper tray assembly and/or the lower tray assembly include at least one channel pillar, and when the upper tray assembly is combined with the lower tray assembly, gaps between the upper tray assembly and the lower tray assembly and the at least one channel pillar jointly form at least one airflow channel.

In one embodiment, the number of the at least one channel pillar is odd.

In one embodiment, the number of the at least one airflow channel is even, and the structure of the at least one airflow channel is symmetrical.

The implementation of a mandibular advancement device with an adjustment part at least includes the following benefits:

1. Mandibular advancement devices typically require precise distance adjustment. Fine adjustment helps to avoid the risks associated with over-adjustment, which can lead to excessive advancement distance. This excessive distance can cause pain and discomfort in the jaw joint and inside the mouth, and may even lead to disorders of the temporomandibular joint, oral ulcers, and other soft tissue injuries. Furthermore, by finely adjusting and gradually increasing the advancement distance, users can more easily adapt to the device, making the wearing process more comfortable and thus improving compliance and willingness to wear. Additionally, the fine adjustment of the advancement distance facilitates a gradual adaptation to the treatment process, ultimately enhancing the therapeutic effectiveness of the device. Although other structures on the market offer fine adjustment, many issues still persist. For instance, while bolt adjustment allows for precise settings, the addition of small parts can lead to bolts loosening. If a bolt falls out, it may enter the esophagus or even the airway, posing significant potential hazards. Another design includes an external connecting arm; if made from rigid materials, it tends to scratch the edges of the mouth, whereas if made from flexible materials, it tends to loosen and fail to secure properly. Gear structures, similar to snap-fit configurations but different in assembly, typically require force to adjust the advancement distance back and forth. Gear structures also need to be made from more rigid materials to prevent loosening or wear, commonly using polycarbonate materials. However, mandibular advancement devices often require the heating of moldable components, and polycarbonate materials can release bisphenol A when heated, which poses health hazards. Moreover, the finer edges of gears make it difficult to align left and right, potentially leading to inconsistent advancement distances that can affect the treatment outcome. To address these issues, this disclosure employs specially designed snap-fit structures, such as I-shaped, F-shaped, E-shaped, and symmetric E-shaped configurations. The special snap-fit design not only ensures the required wall thickness during production but also maintains structural stability. Whether I-shaped, F-shaped, E-shaped, or symmetric E-shaped, these are integral structures secured by snapping together from top to bottom, thus facilitating easier operation during the assembly process. The snap-fit structure of this disclosure provides a more reliable and flexible solution, meeting the needs for precise adjustment of the mandibular advancement distance and ensuring the stability of the device's function, while also making it easier for users to operate and adjust.

2. The disclosure incorporates an integrated snap-fit structure, enabling multi-position adjustment on a single pair of upper and lower frames. This design allows users to adjust the forward movement of the lower tray assembly according to personal needs, selecting the most effective and comfortable position, thereby enhancing the compliance to the mandibular advancement device. Compared to using multiple different combinations of upper and lower frames, this disclosure utilizes specially designed snap-fit structures such as I-shaped, F-shaped, E-shaped, and symmetric E-shaped. A single pair of upper and lower frames can now provide more precise and varied forward adjustment positions. This design not only eliminates the need for multiple frames but also enables more position adjustments on a single frame while ensuring the precision of the adjustment range. This offers a more economical and simpler solution, reducing costs and operational complexity.

3. Existing mandibular advancement devices available on the market still have issues with slipping out during sleep, with many users reporting that the device often detaches from the teeth, leading to device fallout. Testing and analysis have shown that this detachment issue is primarily due to the necessary forward movement of the lower tray assembly relative to the upper tray assembly, combined with possible movements or involuntary mouth opening by the user during sleep, all of which can lead to the device slipping off. To address this issue, the upper and lower tray assemblies need to provide sufficient support in their forward and backward positioning to ensure the device remains securely in place during use. Moreover, each tooth has a certain angular difference and is not necessarily perpendicular to the horizontal plane. For example, the anterior teeth (central and lateral incisors) are usually inclined towards the lip at an angle of about 10° to 25° from the vertical plane; canines (towards the lip side) have an inclination of about 5° to 15°; and molars (towards the lip side) usually have an inclination of 0 to 5°. The anterior teeth and canines have a larger angle relative to the vertical plane, whereas molars have a smaller angle, leading to different support needs when the user bites down. Existing mandibular advancement devices often have frames with inner and outer walls set perpendicular to the bottom walls, a design that does not accommodate the natural shape of the teeth, leading to discomfort and ease of slippage when worn. Another common design of frames of mandibular advancement devices consists only of bottom walls without setting inner and outer walls in the forward and backward position, lacking sufficient support and allowing teeth to easily slide out of the device. After multiple tests with users of various tooth forms, this disclosure provides an improved frame design. The frame provided by this disclosure has inner and outer walls to provide adequate support. Moreover, an angle is formed between the inner walls and the bottom walls to accommodate the natural inclination of the anterior teeth towards the lip, thereby fitting more closely to the shape of the teeth. Through this structural design, the mandibular advancement device provided by this disclosure has shown significant stability in experimental trials, reducing the likelihood of the device falling out. This design also enhances comfort and effectiveness when worn, addressing major issues with existing products.

DETAILED DESCRIPTION

Figure 1:
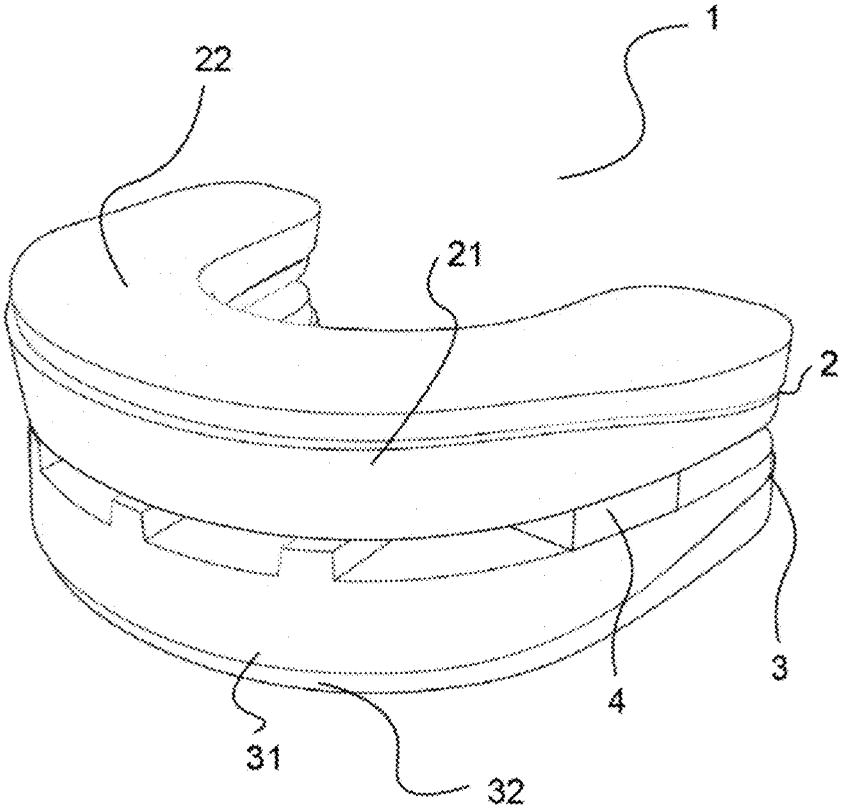
FIG. 1 is a schematic diagram of the structure of a mandibular advancement device in accordance with one embodiment.
Figure 2:
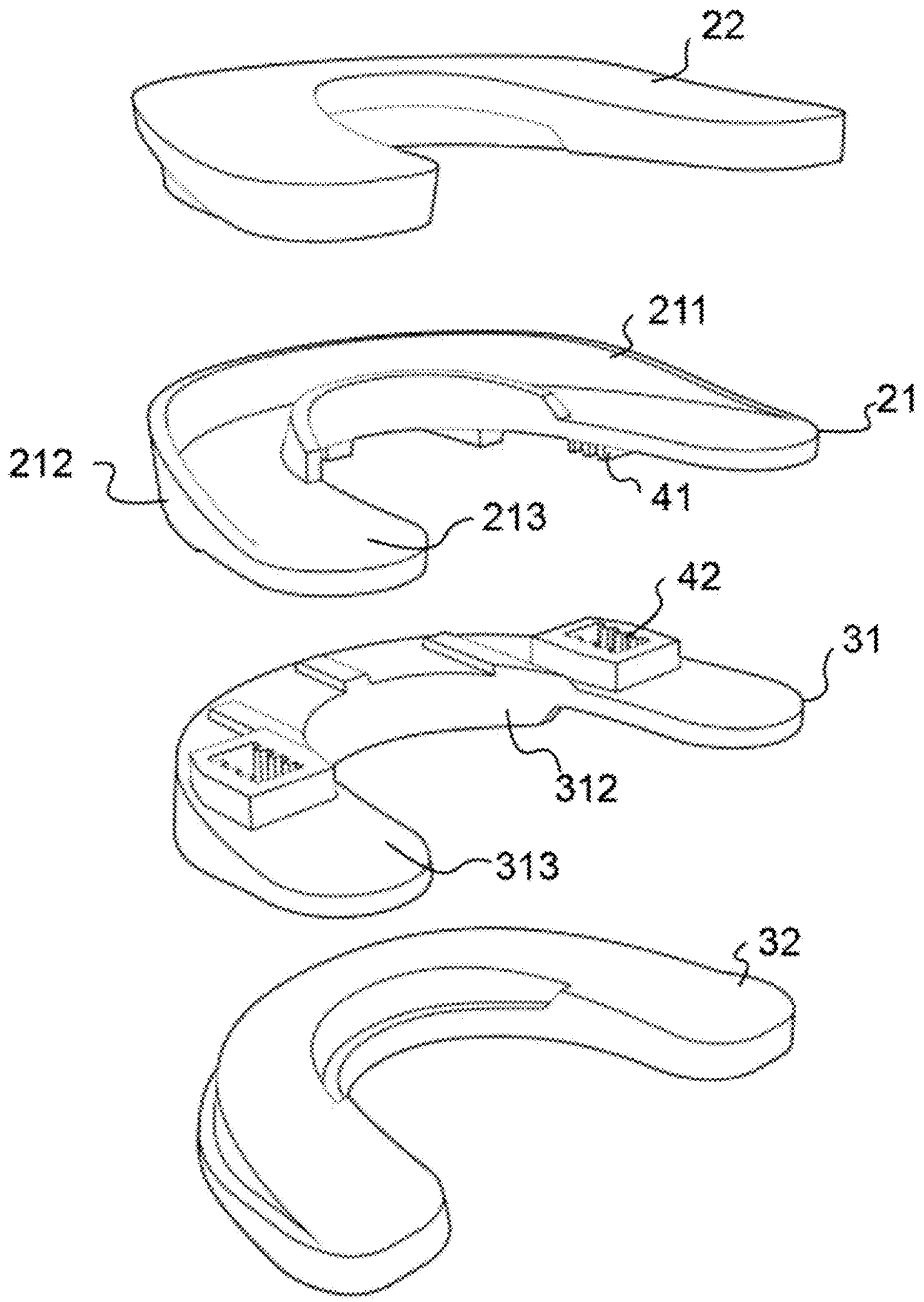
FIG. 2 is an exploded schematic diagram of the structure of a mandibular advancement device in accordance with one embodiment.
Figure 3:
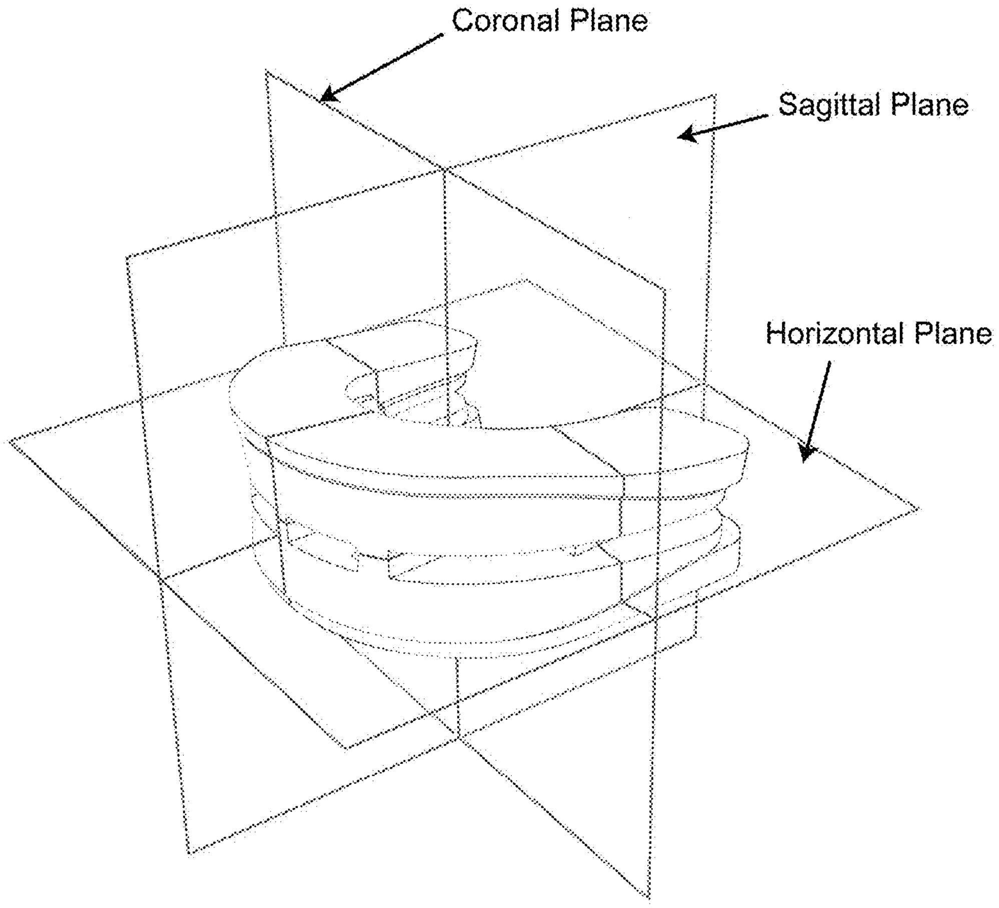
FIG. 3 is a schematic diagram of the horizontal, sagittal, and coronal planes of a mandibular advancement device in accordance with multiple embodiments.
Figure 4:
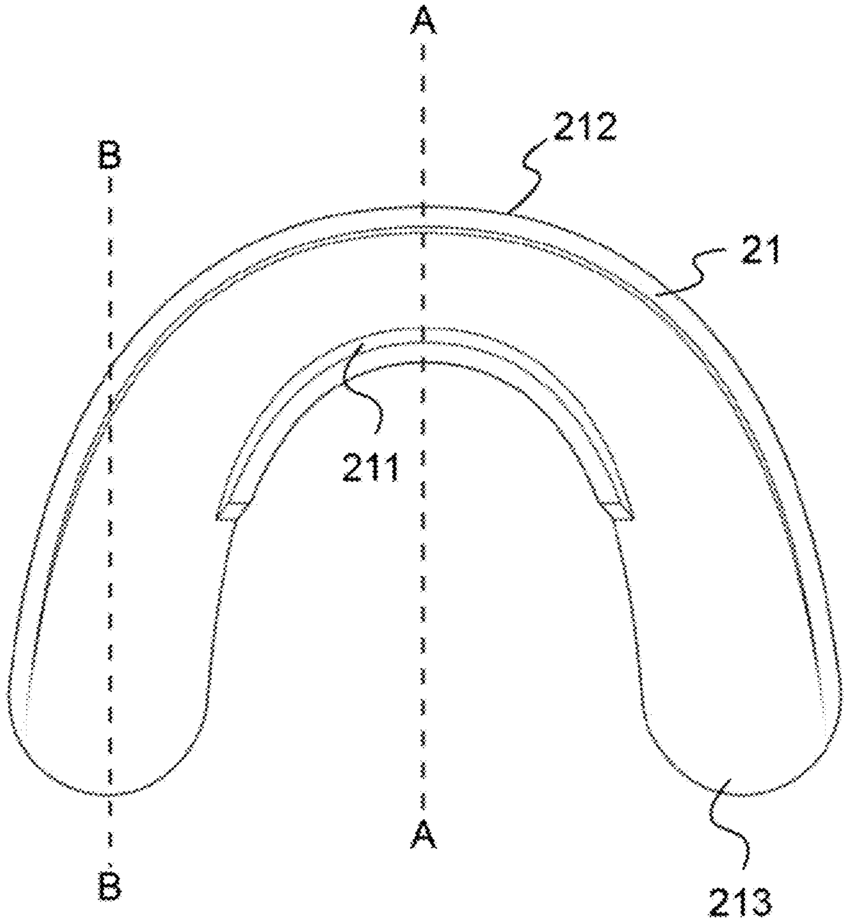
FIG. 4 is a top view of the combination of the upper frame and the lower frame in accordance with multiple embodiments.

To better elucidate the objectives, features, and advantages of this disclosure, a more comprehensive description will be provided with reference to the relevant drawing. The description below contains many specific details to facilitate a comprehensive understanding of the disclosure. However, it is apparent to one skilled in the art that the disclosure may be implemented in many other ways that differ from the specific implementations described here, without departing from the essence of the disclosure. Therefore, the scope of the disclosure is not limited by the specific embodiments disclosed below.

The disclosure provides a mandibular advancement device 1 with an adjustment part 4, including an upper tray assembly 2, a lower tray assembly 3, and an adjustment part 4. The dental arches generally have an arch shape that conforms to the natural arrangement of the user's teeth. Specifically, both the upper dental arch and the lower dental arch form a roughly symmetrical and approximately arch-shaped curvature. Therefore, the upper tray assembly 2 and the lower tray assembly 3 are generally arch-shaped to conform to a curvature of the user's dental arches. The upper tray assembly 2 is configured to contact the user's upper dental arch; the lower tray assembly 3 is configured to contact the user's lower dental arch.

The upper tray assembly 2 and/or the lower tray assembly 3 includes at least two different materials. The material choices for the upper tray assembly 2 and the lower tray assembly 3 are extensive and include plastics or polymers suitable for oral medical devices that can be molded. These materials include, but are not limited to, polypropylene, polycarbonate, polyethylene terephthalate, polymethyl methacrylate, polyphenylsulfone, polyethylene, high-density polyethylene, low-density polyethylene, ethylene-vinyl acetate, thermoplastic polyurethane, styrene-ethylene-butylene-styrene, styrene-ethylene-propylene-styrene, and silicone rubber. Each component of the upper tray assembly 2 and the lower tray assembly 3 can be made from a single material or a combination of materials. This multi-material design leverages the characteristics of different materials to meet various needs during the use of the mandibular advancement device 1. The polymer materials may contain various fillers, plasticizers, stabilizers, pigments, and other additives to meet different performance requirements and manufacturing needs. For example, nanoscale fillers can be added to enhance the material's strength and hardness, or antimicrobial agents can be added to improve the hygiene performance of the oral appliance.

Specifically, referring to FIGS. 1 to 4, the upper tray assembly 2 includes an upper frame 21 and an upper moldable component 22. The upper moldable component 22 includes a flexible thermoplastic material that softens upon heating, allowing it to be adjusted and molded to match the shape of the user's upper dental arch when the user bites down. The upper frame, compared to the upper moldable component, is made at least partially from a relatively rigid material which has a hardness between Shore D45 to Shore D95. The lower tray assembly 3 includes a lower frame 31 and a lower moldable component 32. The lower moldable component 32, made from a flexible thermoplastic material, softens upon heating to be adjusted and molded to match the shape of the user's lower dental arch when the user bites down. The lower frame, compared to the lower moldable component, is also made at least partially from a relatively rigid material which has a hardness between Shore D45 to Shore D95. In this disclosure, the tray assemblies 2, 3 include the upper tray assembly 2 and the lower tray assembly 3, frames 21, 31 include the upper frame 21 and the lower frame 31, and moldable components 22, 32 include the upper moldable component 22 and the lower moldable component 32.

The disclosure allows for simple heating methods to adjust the fit of the mandibular advancement device 1, with the preferred method being a "boil-and-bite" process. Users only need to heat the mandibular advancement device 1 in hot water, then lightly bite down on it to form a good fit with their teeth.

The moldable components 31, 32 soften upon heating, allowing users to easily adjust and adapt during the initial fitting of the mandibular advancement device 1. This simple heating method enables users without specialized skills to conveniently make fit adjustments themselves, thereby enhancing comfort and wearing experience.

Frames 21 and 31 of the mandibular advancement device 1 are made from relatively rigid materials to ensure the overall structural stability and support of the device, while the moldable components 22 and 32 are made from thermoplastic materials, offering comfort and malleability. To ensure stability during use, the materials for frames 21 and 31 have a higher heat deformation temperature compared to moldable components 22 and 32, preventing any structural impact on the frames during the heating process. This selection of material combinations is configured to enhance both stability and comfort, ensuring appropriate adjustments can be made to conform to the dental arch during use.

Figure 5:
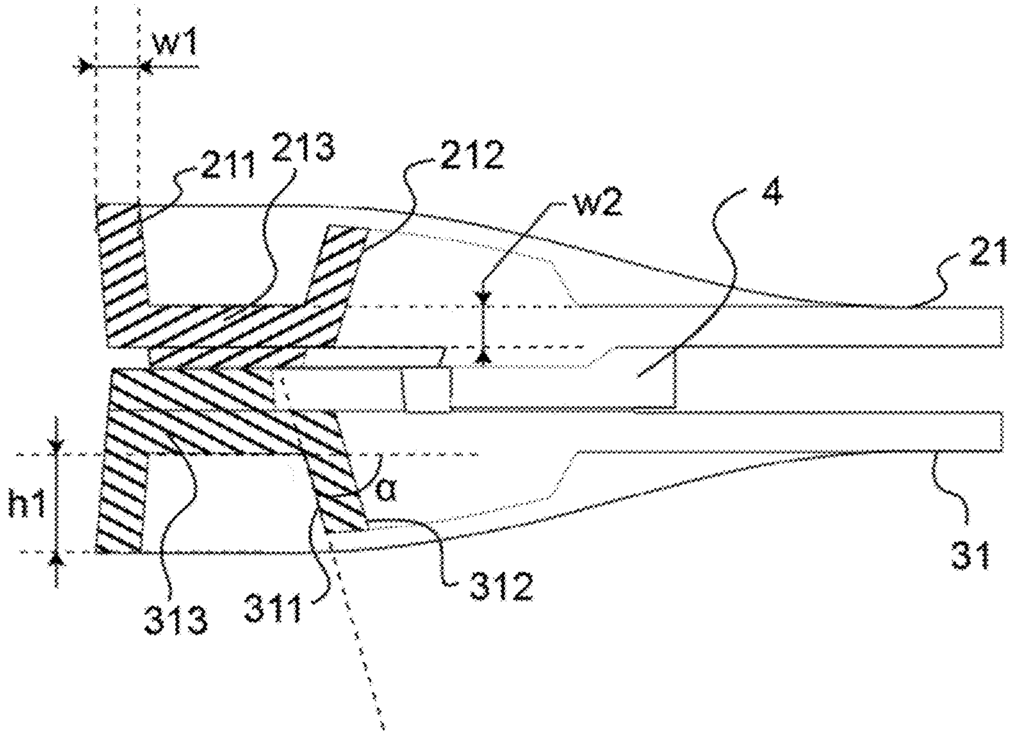
FIG. 5 is a cross-sectional view along line A-A in FIG. 3 of the frame in accordance with one embodiment.
Figure 6A:
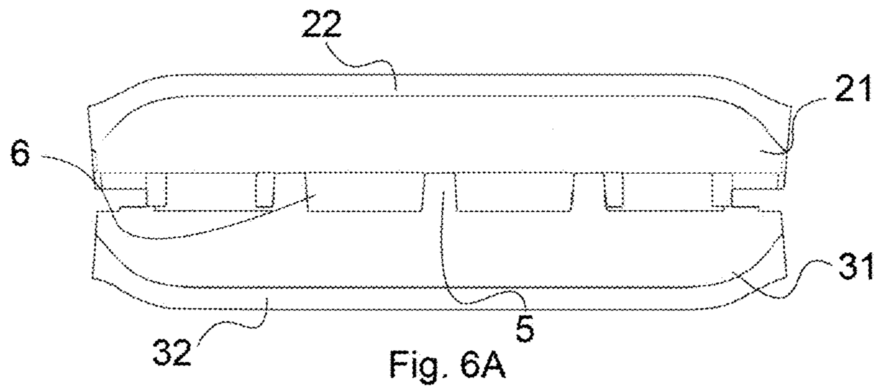
FIGS. 6A, 6B and 6C are schematic diagrams showing the positions of the at least one channel pillar in a mandibular advancement device in accordance with one embodiment.
Figure 6B:
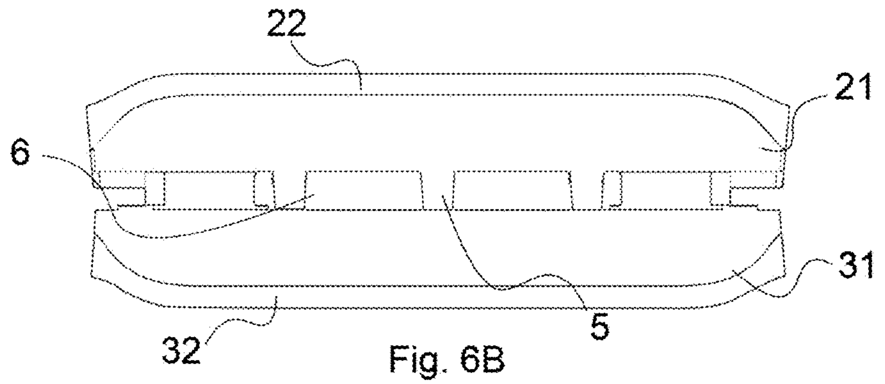
Figure 6C:
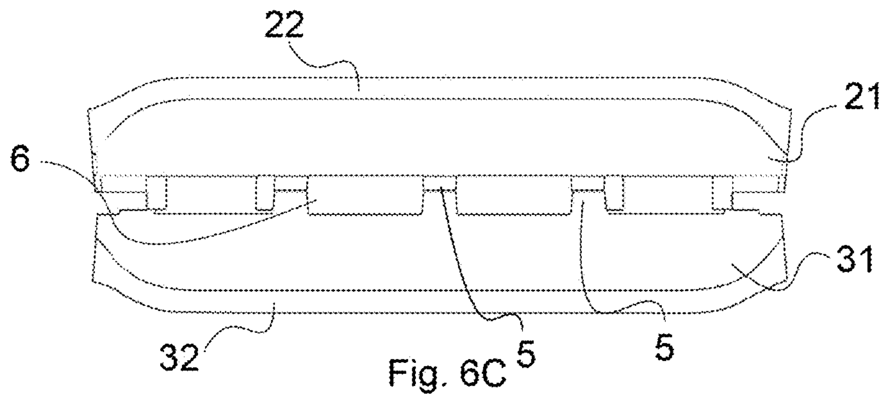
Figures 7A, 7B, 7C, 7D:
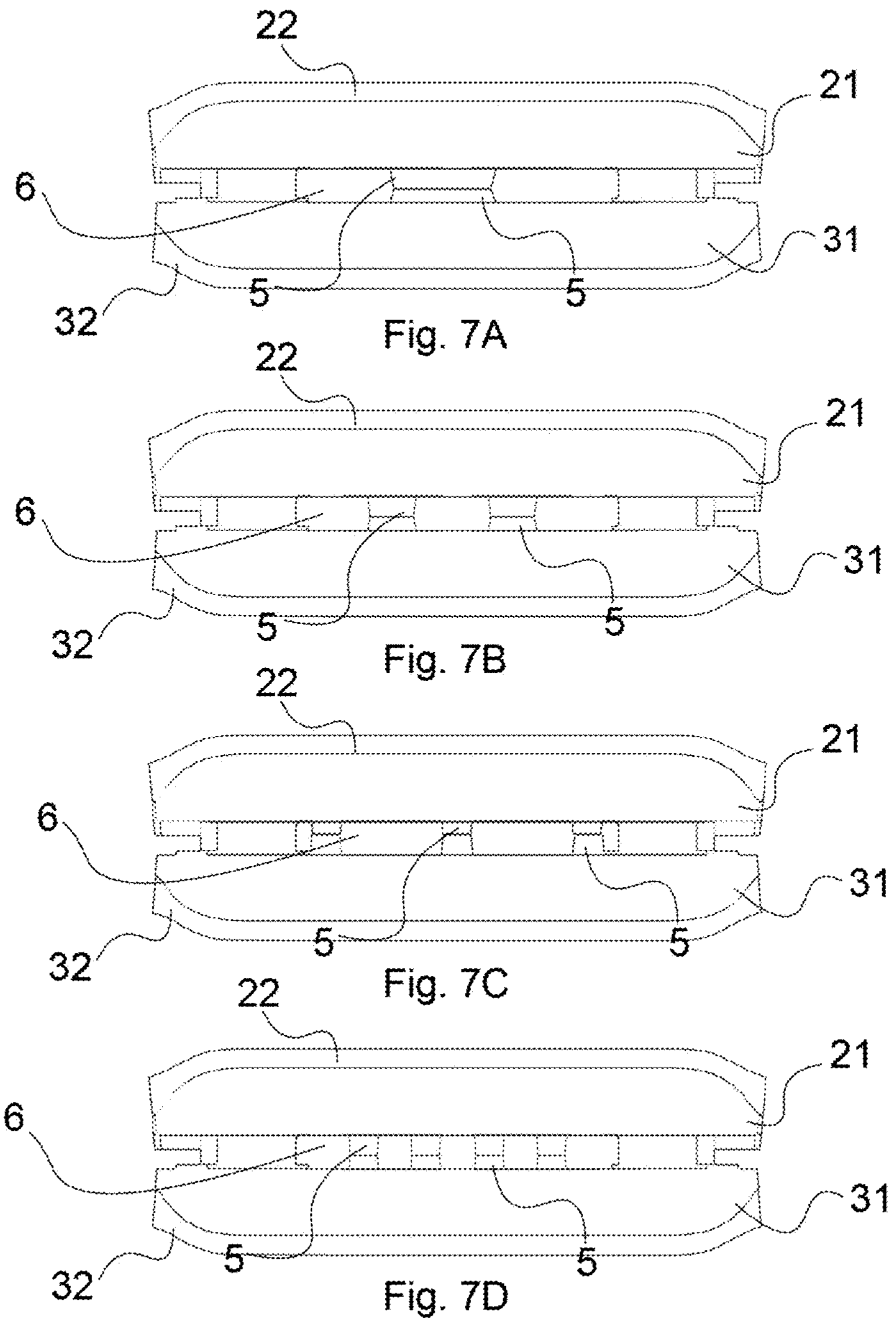
FIGS. 7A, 7B, 7C and 7D are schematic diagrams showing the number of at least one channel pillar in a mandibular advancement device in accordance with one embodiment.

Further enhancing user comfort, the mandibular advancement device 1 provided by this disclosure uses lightweight materials. As shown in FIG. 5, frames 21 and 31 have inner walls 211 and 311, outer walls 212 and 312, and bottom walls 213 and 313. The overall weight of the frames is between 3 g to 50 g, and the total weight of the mandibular advancement device 1 is between 8 g to 80 g. The distance between inner walls 211, 311, and outer walls 212, 312 is partially between 0.3 mm to 8 mm, labeled as w1 in FIG. 5, and the thickness of bottom walls 213, 313 is between 0.5 mm and 20 mm, labeled as w2 in FIG. 5. Preferably, the distance between inner walls 211, 311 and outer walls 212, 312 is between 1 mm and 1.6 mm, and the thickness of bottom walls 213, 313 is between 1 mm and 2 mm. This design ensures the necessary support and rigidity for the mandibular advancement device 1, while avoiding excessive weight of the frames, thereby reducing the oral burden and enhancing comfort.

Existing mandibular advancement devices 1 available on the market still have issues with slipping out during sleep, with many users reporting that the device 1 often detaches from the teeth, leading to device fallout. Testing and analysis have shown that this detachment issue is primarily due to the necessary forward movement of the lower tray assembly 3 relative to the upper tray assembly 2, combined with possible movements or involuntary mouth opening by the user during sleep, all of which can lead to the device 1 slipping off. To address this issue, the upper and lower tray assemblies 2, 3 need to provide sufficient support in their forward and backward positioning to ensure the device remains securely in place during use. Moreover, each tooth has a certain angular difference and is not necessarily perpendicular to the horizontal plane. For example, the anterior teeth (central and lateral incisors) are usually inclined towards the lip at an angle of about 10° to 25° from the vertical plane; canines (towards the lip side) have an inclination of about 5° to 15°; and molars (towards the lip side) usually have an inclination of 0 to 5°. The anterior teeth and canines have a larger angle relative to the vertical plane, whereas molars have a smaller angle, leading to different support needs when the user bites down. Existing mandibular advancement devices often have frames with inner and outer walls set perpendicular to the bottom walls, a design that does not accommodate the natural shape of the teeth, leading to discomfort and ease of slippage when worn. Another common design of frames of mandibular advancement devices consists only of bottom walls without setting inner and outer walls in the forward and backward position, lacking sufficient support and allowing teeth to easily slide out of the device. After multiple tests with users of various dental forms, this disclosure provides an improved frame design as shown in FIG. 5. Frames 21 and 31 have inner walls 211 and 311 and outer walls 212 and 312 to provide adequate support. The vertical distance between inner walls 211, 311, outer walls 212, 312, and bottom walls 213, 313 is between 0.5 mm to 20 mm, labeled as h1 in FIG. 5, the total circumference of the outer walls 212, 312 ranges from 2 mm to 200 mm, and the total area of the outer walls 212, 312 ranges from 50 $mm^2$ to 2000 $mm^2$. Additionally, the inner walls 211 and 311 of the frames form an angle between 20° to 150° with the horizontal plane, directed towards the corresponding outer walls 212 and 312, respectively. For example, the inner wall 311 forms an angle between 20° to 150° with the horizontal plane, directed towards the corresponding outer wall 312. This angle is designated as angle $\alpha$ in FIG. 5. This angle adapts to the natural inclination of the anterior teeth towards the lip side, thus fitting more closely to the shape of the teeth. Preferably, the angle between the inner walls 211, 311 and the horizontal plane ranges from 45° to 90°. Through this structural design, the mandibular advancement device 1 of this disclosure has shown significant stability in experimental trials, reducing the possibility of falling out of the device. This design also enhances the comfort and effectiveness of wear, solving major issues with existing products.

The upper tray assembly 2 and/or the lower tray assembly 3 includes at least one channel pillar 5. As shown in FIGS. 6A, 6B, 6C and FIGS. 7A, 7B, 7C, 7D, in this disclosure, the at least one channel pillar 5 provided at the same position are all part of the same channel pillar 5. At least one channel pillar 5 can be entirely provided on the upper tray assembly 2, entirely on the lower tray assembly 3, or partly on the upper tray assembly 2 and partly on the lower tray assembly 3. When the upper tray assembly 2 is combined with the lower tray assembly 3, the tray assemblies 2, 3, and the at least one channel pillar 5 together form at least one airflow channel 6. The height of the at least one channel pillar 5 is between 0.5 mm to 25 mm, while the area of the at least one airflow channel 6 ranges from 2 $mm^2$ to 500 $mm^2$. Thus, when the user wears the mandibular advancement device 1, the device does not close completely, allowing external airflow to enter the user's mouth through the at least one airflow channel 6 without restricting the free flow of air within the mouth. This also meets the needs of users who habitually breathe through their mouths during sleep, avoiding the risk of suffocation.

Further, the number of at least one channel pillar 5 is odd to ensure that there is always a channel pillar 5 at the center of the mandibular advancement device 1 (i.e., the position of the user's anterior teeth). At least one channel pillar 5 on both sides separates out the at least one airflow channel 6, therefore, the number of at least one airflow channel 6 is even and structured symmetrically. When the upper and lower teeth bite together, since the anterior teeth are typically longer and usually the first to contact each other, they bear more pressure. Placing a channel pillar 5 at the center of the mandibular advancement device 1 helps the device 1 withstand greater pressure and contributes to the stability of the device 1. Moreover, the symmetrical structure of the at least one airflow channel 6 helps stabilize the airflow passing through, further enhancing the safety and stability of the mandibular advancement device 1.

Figure 8:
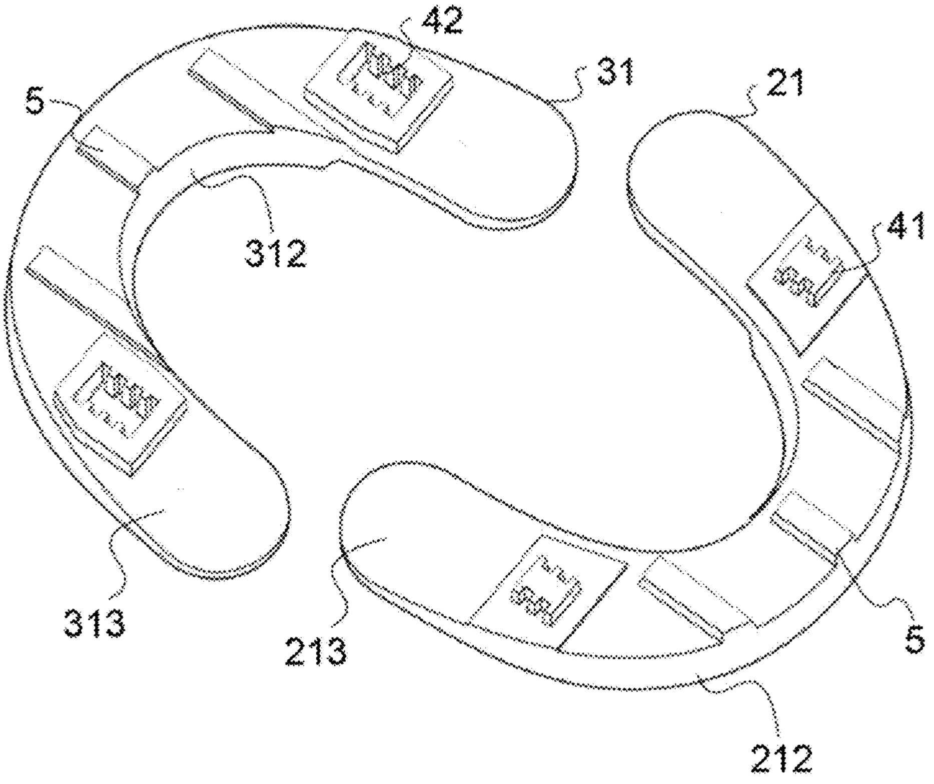
FIG. 8 is a schematic diagram of the disassembly of the upper frame and the lower frame in accordance with one embodiment.
Figure 9:
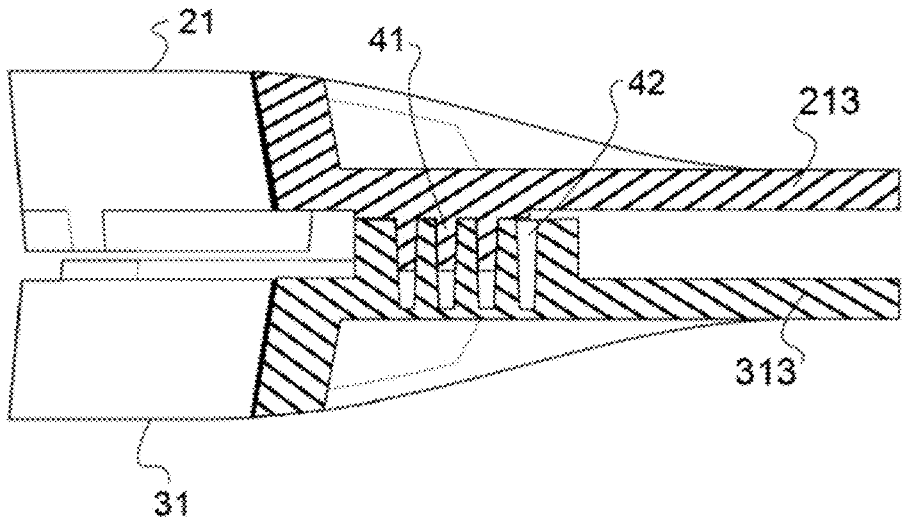
FIG. 9 is a cross-sectional view along line B-B in FIG. 3 of the frame in accordance with one embodiment.

The adjustment part 4 is configured to connect the upper tray assembly 2 and the lower tray assembly 3 using a snap-fit, and to adjust the position of the lower tray assembly 3 relative to the upper tray assembly 2. As shown in FIGS. 8 and 9, the snap-fit specifically involves at least one protrusion 41 on one side of the upper tray assembly 2 and/or the lower tray assembly 3. The at least one protrusion 41 is configured to compressively connect the upper frame 21 and the lower frame 31. The adjustment part 4 includes the at least one protrusion 41 and at least one protrusion receiving part 42, and can adjust multiple positions.

Figure 10:
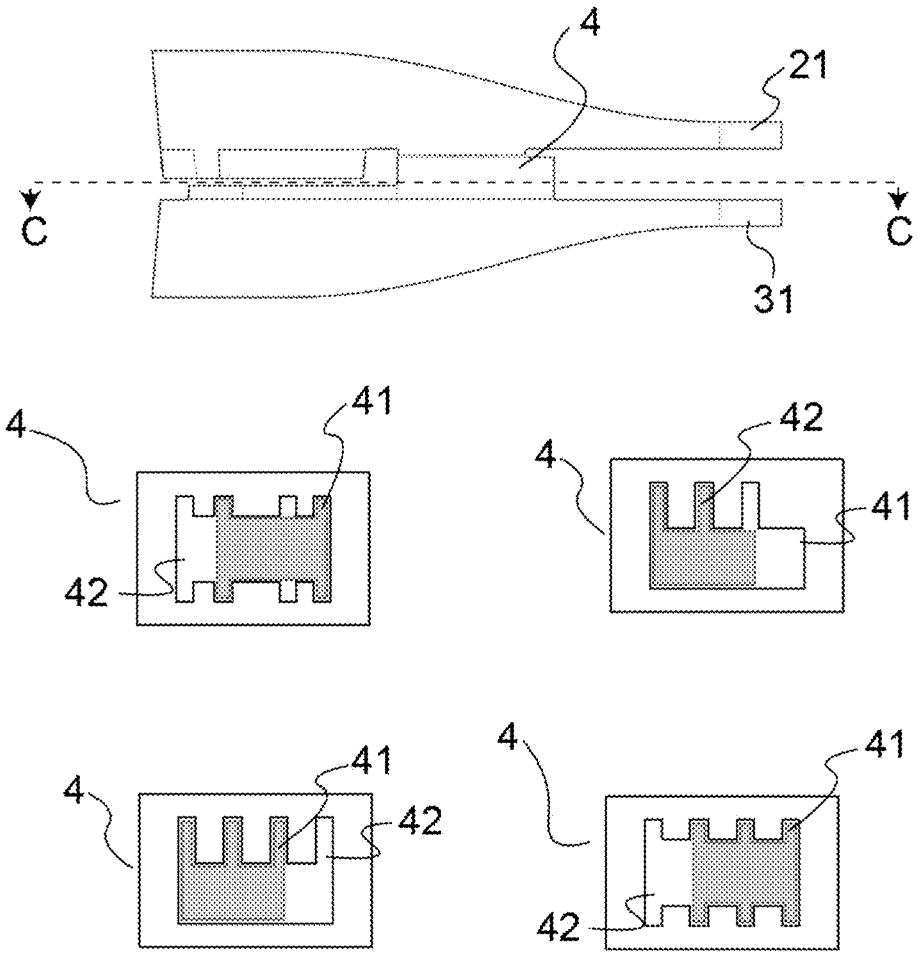
FIG. 10 is a cross-sectional schematic diagram of the shapes of the adjustment part in accordance with one embodiment.
Figure 12:
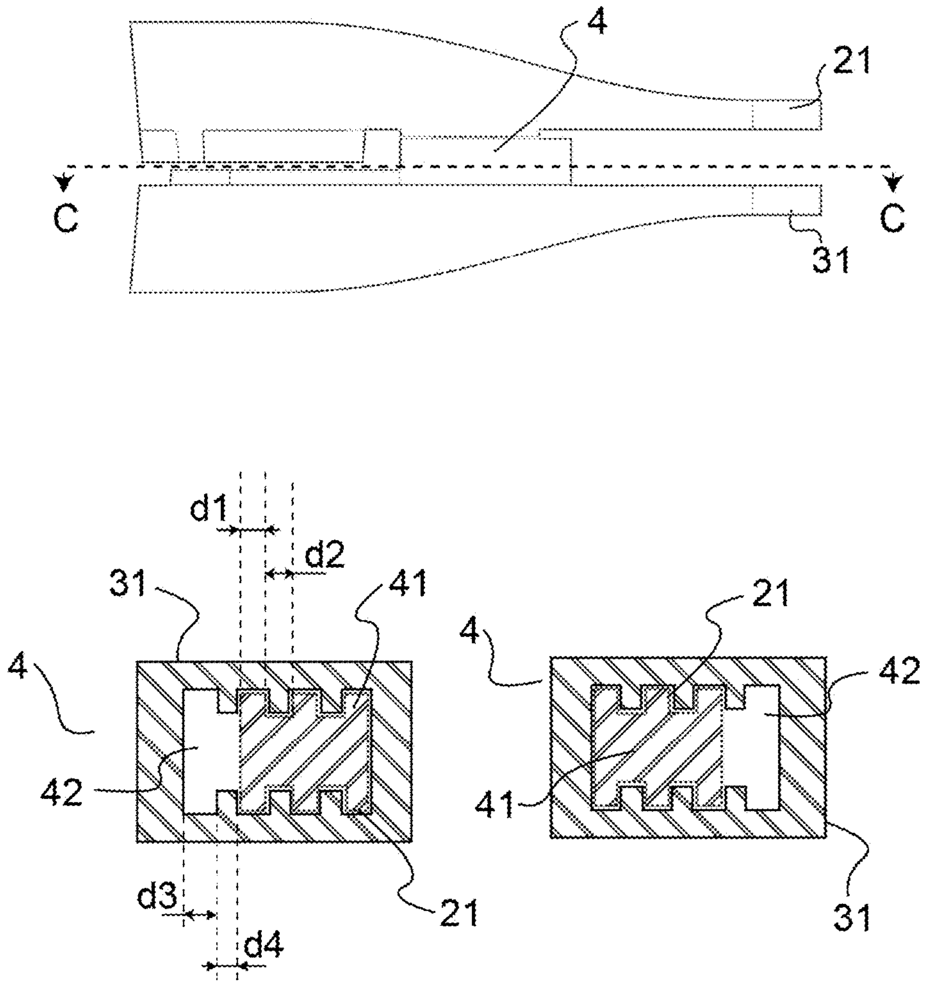
FIG. 12 is a cross-sectional schematic diagram of the adjustment part in accordance with one embodiment.

Specifically, as shown in FIG. 10, the adjustment part 4, including the at least one protrusion 41 and the at least one protrusion receiving part 42, is configured in shapes such as I-shaped, F-shaped, E-shaped, or symmetric E-shaped. Mandibular advancement devices 1 typically require precise distance adjustment. Fine adjustment helps to avoid the risks associated with over-adjustment, which can lead to excessive advancement distance. This excessive distance can cause pain and discomfort in the jaw joint and inside the mouth, and may even lead to disorders of the temporomandibular joint, oral ulcers, and other soft tissue injuries. Furthermore, by finely adjusting and gradually increasing the advancement distance, users can more easily adapt to the device, making the wearing process more comfortable and thus improving compliance and willingness to wear. Additionally, the fine adjustment of the advancement distance facilitates a gradual adaptation to the treatment process, ultimately enhancing the therapeutic effectiveness of the device. Although other structures on the market offer fine adjustment, many issues still persist. For instance, while bolt adjustment allows for precise settings, the addition of small parts can lead to bolts loosening. If a bolt falls out, it may enter the esophagus or even the airway, posing significant potential hazards. Another design includes an external connecting arm; if made from rigid materials, it tends to scratch the edges of the mouth, whereas if made from flexible materials, it tends to loosen and fail to secure properly. Gear structures, similar to snap-fit configurations but different in assembly, typically require force to adjust the advancement distance back and forth. Gear structures also need to be made from more rigid materials to prevent loosening or wear, commonly using polycarbonate materials. However, mandibular advancement devices 1 often require the heating of moldable components, and polycarbonate materials can release bisphenol A when heated, which poses health hazards. Moreover, the finer edges of gears make it difficult to align left and right, potentially leading to inconsistent advancement distances that can affect the treatment outcome. To address these issues, this disclosure employs specially designed snap-fit structures, such as I-shaped, F-shaped, E-shaped, and symmetric E-shaped configurations. The special snap-fit design not only ensures the required wall thickness during production but also maintains structural stability. Whether I-shaped, F-shaped, E-shaped, or symmetric E-shaped, these are integral structures secured by snapping together from top to bottom, thus facilitating easier operation during the assembly process. The snap-fit structure of this disclosure provides a more reliable and flexible solution, meeting the needs for precise adjustment of the mandibular advancement distance and ensuring the stability of the device 1's function, while also making it easier for users to operate and adjust. As seen in FIG. 10, the upper frame 21 and lower frame 31 are spaced in the vertical direction. The protrusions 41 are retained in the protrusion receiving part 42 in either a first predetermined position or a second predetermined position by the nonplanar sidewalls extending in a horizontal direction interlocking with each other. The two predetermined positions are offset from each other in the horizontal direction. The two predetermined positions are also seen in FIG. 12. The protrusions 41 and the protrusion receiving part 42 prevent relative movement of the upper frame and lower frame in a horizontal direction.

This disclosure employs an integrated snap-fit structure, enabling multi-position adjustment on a single pair of upper and lower frames 21 and 31. This design allows users to adjust the forward movement of the lower tray component 3 according to personal needs, selecting the most effective and comfortable position, thereby enhancing the compliance to the mandibular advancement device 1. Compared to using multiple different combinations of upper and lower frames, this disclosure utilizes specially designed snap-fit structures such as I-shaped, F-shaped, E-shaped, and symmetric E-shaped. A single pair of upper and lower frames 21 and 31 can now provide more precise and varied forward adjustment positions. This design not only eliminates the need for multiple frames but also enables more position adjustments on a single pair of frames 21 and 31 while ensuring the precision of the adjustment range. This innovation offers a more economical and simpler solution, significantly reducing costs and operational complexity.

Detailed embodiments are presented below to elucidate the configurations of the mandibular advancement device 1 with an adjustment part 4.

Embodiment 1

In this embodiment, a mandibular advancement device 1 includes an upper tray assembly 2, a lower tray assembly 3, and an adjustment part 4. The upper tray assembly 2 and the lower tray assembly 3 are generally arch-shaped to conform to the curvature of a user's dental arch. Specifically, the upper tray assembly 2 includes an upper frame 21 and an upper moldable component 22, while the lower tray assembly 3 includes a lower frame 31 and a lower moldable component 32. The adjustment part 4 is configured to connect the upper tray assembly 2 to the lower tray assembly 3 using a snap-fit, as well as to adjust the position of the lower tray assembly 3 relative to the upper tray assembly 2. This snap-fit involves at least one protrusion 41 on one side of the upper tray assembly 2 and/or the lower tray assembly 3, and the at least one protrusion 41 is configured to compressively connect the upper frame 21 to the lower frame 31. The adjustment part 4 includes the at least one protrusion 41 and at least one protrusion receiving part 42. In this embodiment, the tray assemblies 2 and 3 include the upper tray assembly 2 and the lower tray assembly 3, the frames 21 and 31 include the upper frame 21 and the lower frame 31, and the moldable components 22 and 32 include the upper moldable component 22 and the lower moldable component 32.

Figure 11:
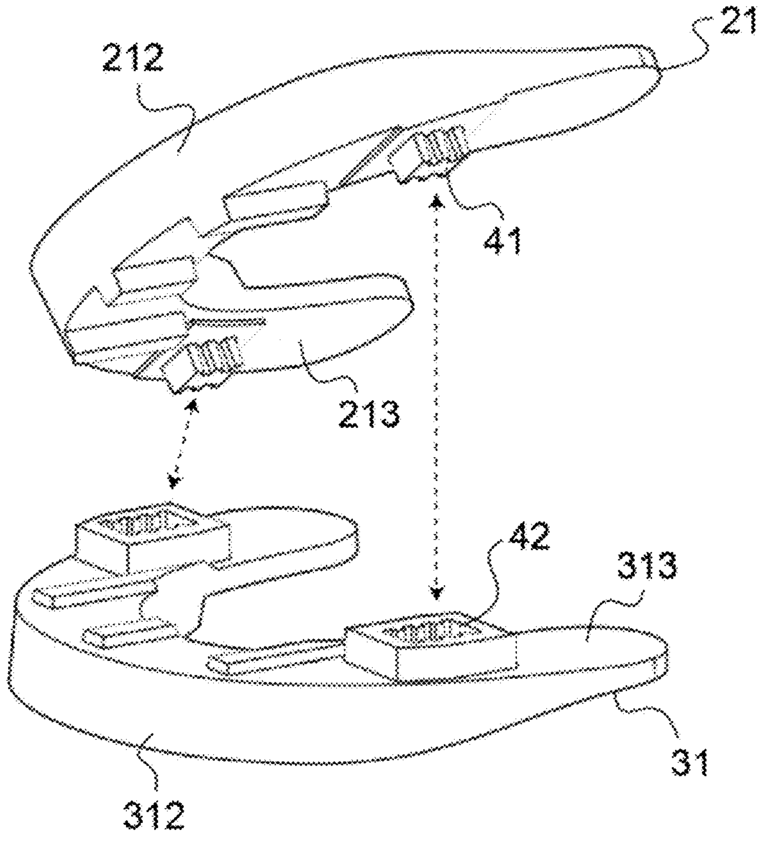
FIG. 11 is an exploded schematic diagram of the structure of a mandibular advancement device in accordance with one embodiment.

As shown in FIG. 11, the frames 21 and 31 have inner walls 211 and 311, as well as outer walls 212 and 312. Here, the at least one protrusion 41 is provided on the surface of the outer wall 212 of the upper frame 21, and the at least one protrusion receiving part 42 is provided on the surface of the outer wall 312 of the lower frame 31, positioned opposite to the at least one protrusion 41.

Figure 14:
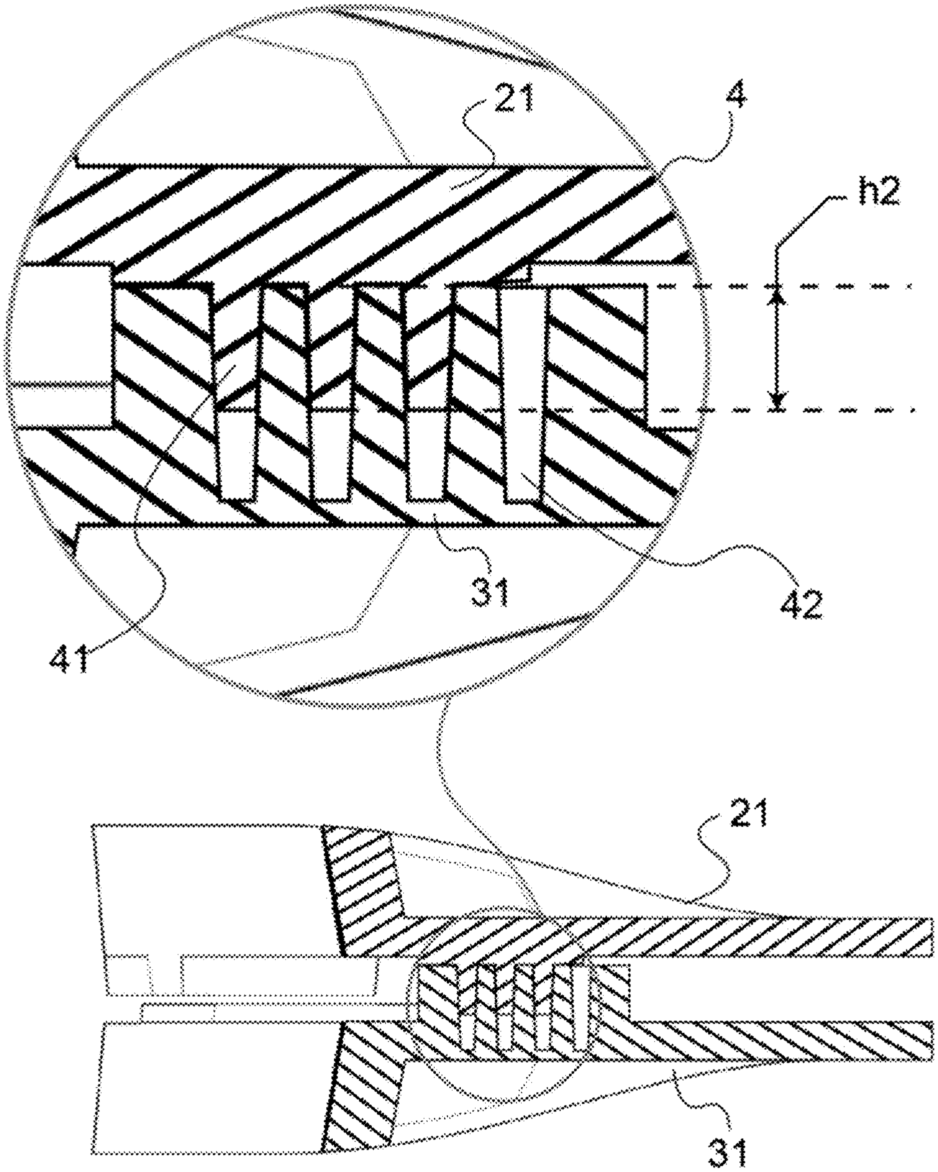
FIG. 14 is an enlarged cross-sectional schematic diagram of the adjustment part in accordance with one embodiment.

In this embodiment, each adjustment position advances the position by 2 mm and the protrusion 41 is set in a symmetric E-shape, not only to achieve more stable fixation but also to ensure that the protrusion 41 and the protrusion receiving part 42 are easy to manufacture and less likely to break. As shown in FIG. 12, the overall width of the protrusion 41 is 5 mm, and its total length is also 5 mm. Each protruding edge of the E-shaped protrusion measures 1 mm, denoted as d1 in FIG. 12, and each recessed edge measures 1 mm, denoted as d2 in FIG. 12. Each position movement thus advances the forward distance by 2 mm, which equals d1+d2. Similarly, the protrusion receiving part 42 corresponds to the protrusion 41 and features a symmetric E-shaped groove. Each protruding edge of the E in the receiving part measures d3 as shown in FIG. 12, and each recessed edge measures d4 in FIG. 12. The dimension d1 of the protrusion 41 corresponds to d3 of the protrusion receiving part 42, and d2 corresponds to d4, with the ratios of d3 to d1 and d4 to d2 designed to be between 1 and 1.2 for better fixation and assembly. Furthermore, once the protrusion 41 and the protrusion receiving part 42 are connected, the overlapping height, as shown in FIG. 14, ranges from 0.5 mm to 20 mm, labeled as h2. Insufficient overlap can cause the protrusion 41 and the protrusion receiving part 42 to separate easily, while excessive overlap can require a greater distance of vertical movement to disengage, which is not convenient for operation. Therefore, the preferred overlapping height is 3 mm.

Figure 13:
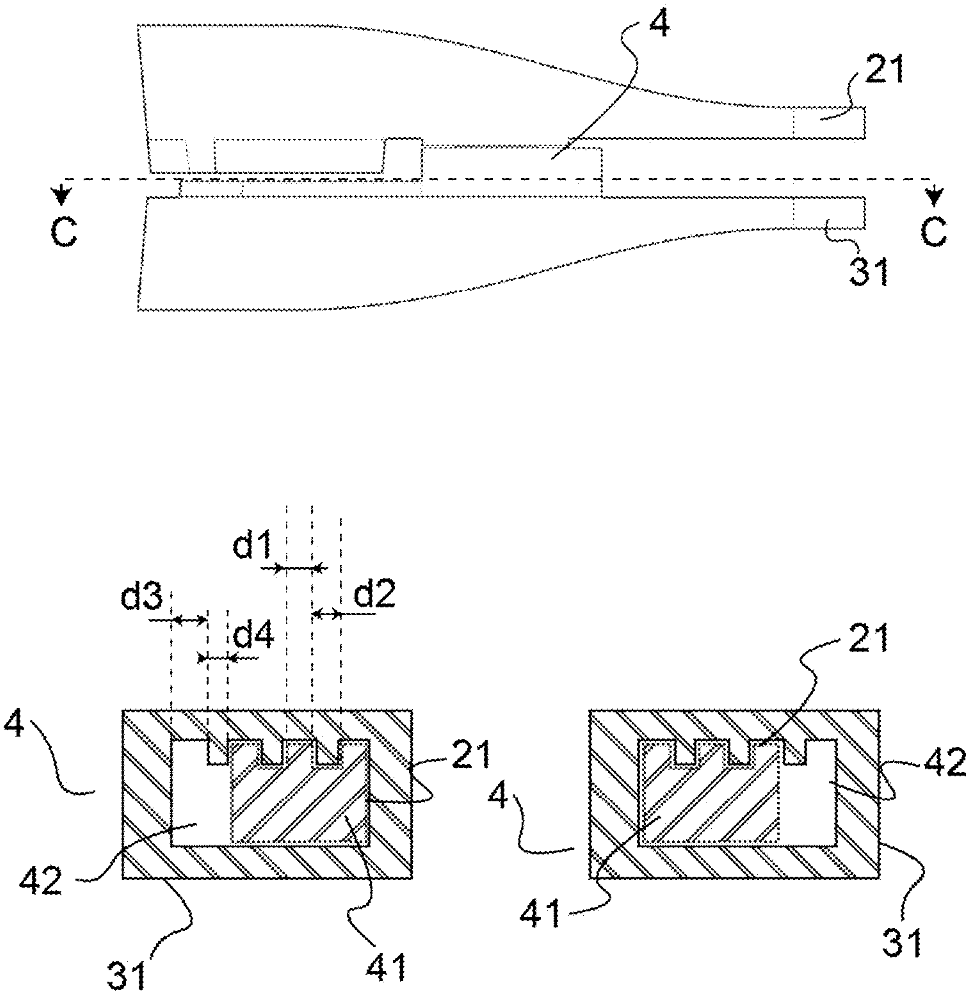
FIG. 13 is a cross-sectional schematic diagram of the adjustment part in accordance with one embodiment.

In other embodiments, the protrusion 41 and the protrusion receiving part 42 are made of metal or another material with a thin wall thickness capable of robust connection, and each adjustment position can be set to less than 2 mm, allowing for finer distance adjustment. For example, the protrusion 41 can have a shape of E, as depicted in FIG. 13. In one configuration, each E's protruding edge is 0.5 mm in length, labeled as d1 in FIG. 13, and each recessed edge also is 0.5 mm in length, labeled as d2 in FIG. 13. Each time an adjustment position is moved, the movement distance is 1 mm, which is the sum of d1 and d2. Similarly, the protrusion receiving part 42 corresponds to the protrusion 41 with an E-shaped groove. The length of each E's protruding edge is denoted as d3 in FIG. 13, and the length of the recessed edge is labeled as d4 in FIG. 13.

Embodiment 2

This embodiment of the mandibular advancement device 1 includes an upper tray assembly 2, a lower tray assembly 3, and an adjustment part 4. The upper tray assembly 2 and the lower tray assembly 3 are generally arch-shaped to conform to the user's dental arch curvature. Specifically, the upper tray assembly 2 includes an upper frame 21 and an upper moldable component 22, while the lower tray assembly 3 comprises a lower frame 31 and a lower moldable component 32. The adjustment part 4 is configured to connect the upper tray assembly 2 to the lower tray assembly 3 using a snap-fit, and to adjust the position of the lower tray assembly 3 relative to the upper tray assembly 2. In this configuration, the snap-fit mechanism involves at least one protrusion 41 on one side of either the upper tray assembly 2 and/or the lower tray assembly 3, and the at least one protrusion 41 is configured to compressively connect the upper frame 21 to the lower frame 31. The adjustment part 4 includes the at least one protrusion 41 and at least one protrusion receiving part 42. In this implementation, the tray assemblies 2 and 3 include the upper tray assembly 2 and the lower tray assembly 3, the frames 21 and 31 include the upper frame 21 and the lower frame 31, and the moldable components 22 and 32 include the upper moldable component 22 and the lower moldable component 32.

Figure 15:
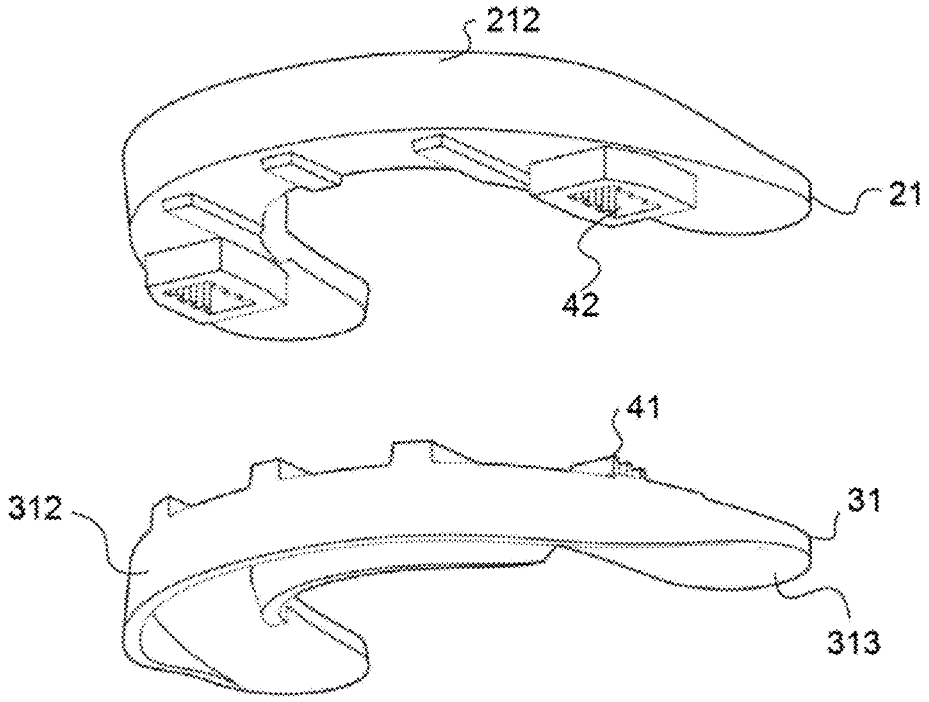
FIG. 15 is an exploded schematic diagram of the structure of a mandibular advancement device in accordance with one embodiment.

This embodiment differs from Embodiment 1 in that the protrusion 41 and the protrusion receiving part 42 of the adjustment part 4 are set in reverse positions. As illustrated in FIG. 15, the frames 21 and 31 have inner walls 211 and 311, as well as outer walls 212 and 312. Here, the at least one protrusion 41 is provided on the surface of the outer wall 312 of the lower frame 31, and the at least one protrusion receiving part 42 is provided on the surface of the outer wall 212 of the upper frame 21, positioned opposite the at least one protrusion 41. This reversed setup enhances the ease of connection and disconnection, optimizing the device's functional adjustments and user comfort.

Figure 16:
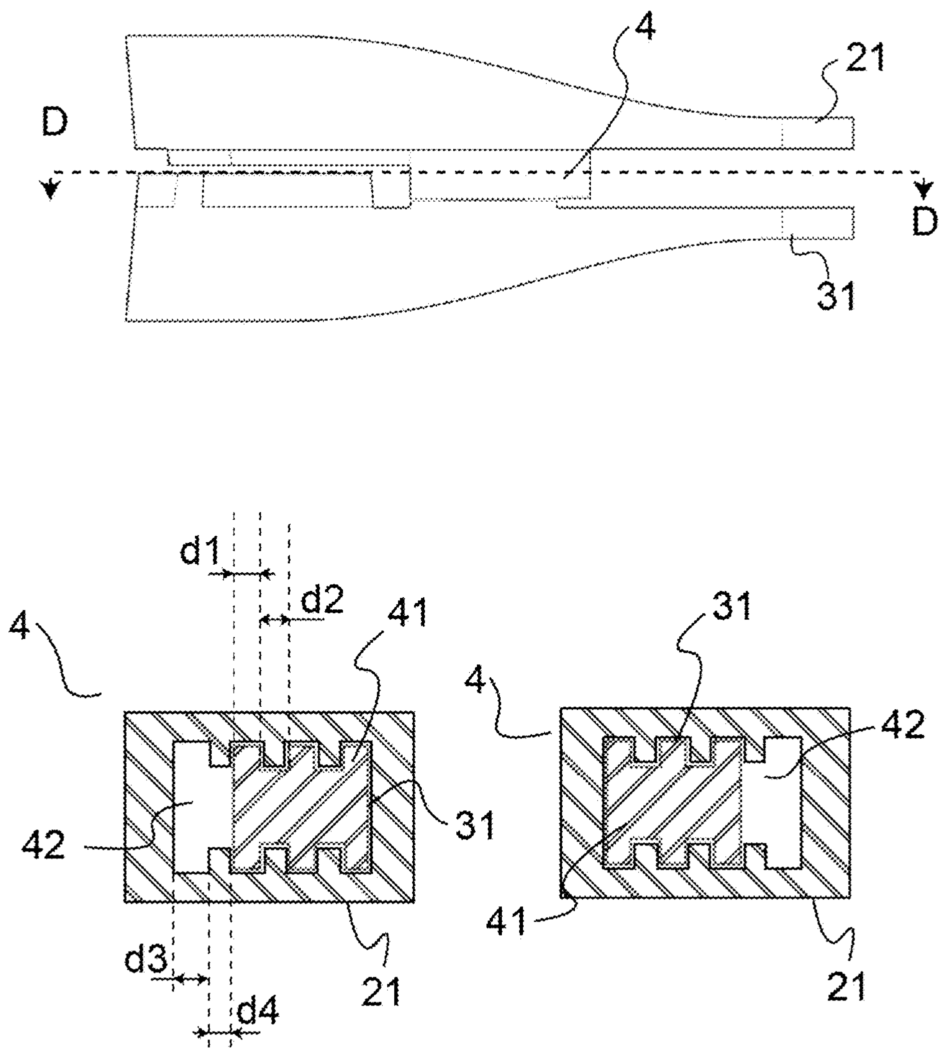
FIG. 16 is a cross-sectional schematic diagram of the adjustment part in accordance with one embodiment.

In this embodiment, each adjustment position advances the position by 2 mm and the protrusion 41 is set in a symmetric E-shape, not only to achieve more stable fixation but also to ensure that the protrusion 41 and the protrusion receiving part 42 are easy to manufacture and less likely to break. As shown in FIG. 16, the overall width of the protrusion 41 is 5 mm, and its total length is also 5 mm. Each protruding edge of the E-shaped protrusion measures 1 mm, denoted as d1 in FIG. 16, and each recessed edge measures 1 mm, denoted as d2 in FIG. 16. Each position movement thus advances the forward distance by 2 mm, which equals d1+d2. Similarly, the protrusion receiving part 42 corresponds to the protrusion 41 and features a symmetric E-shaped groove. Each protruding edge of the E in the receiving part measures d3 as shown in FIG. 16, and each recessed edge measures d4 in FIG. 16. The dimension d1 of the protrusion 41 corresponds to d3 of the protrusion receiving part 42, and d2 corresponds to d4, with the ratios of d3 to d1 and d4 to d2 designed to be between 1 and 1.2 for better fixation and assembly. Furthermore, once the protrusion 41 and the protrusion receiving part 42 are connected, the overlapping height, as shown in FIG. 14, ranges from 0.5 mm to 20 mm, labeled as h2. Insufficient overlap can cause the protrusion 41 and the protrusion receiving part 42 to separate easily, while excessive overlap can require a greater distance of vertical movement to disengage, which is not convenient for operation. Therefore, the preferred overlapping height between the protrusion 41 and the protrusion receiving part 42 is 3 mm.

Figure 17:
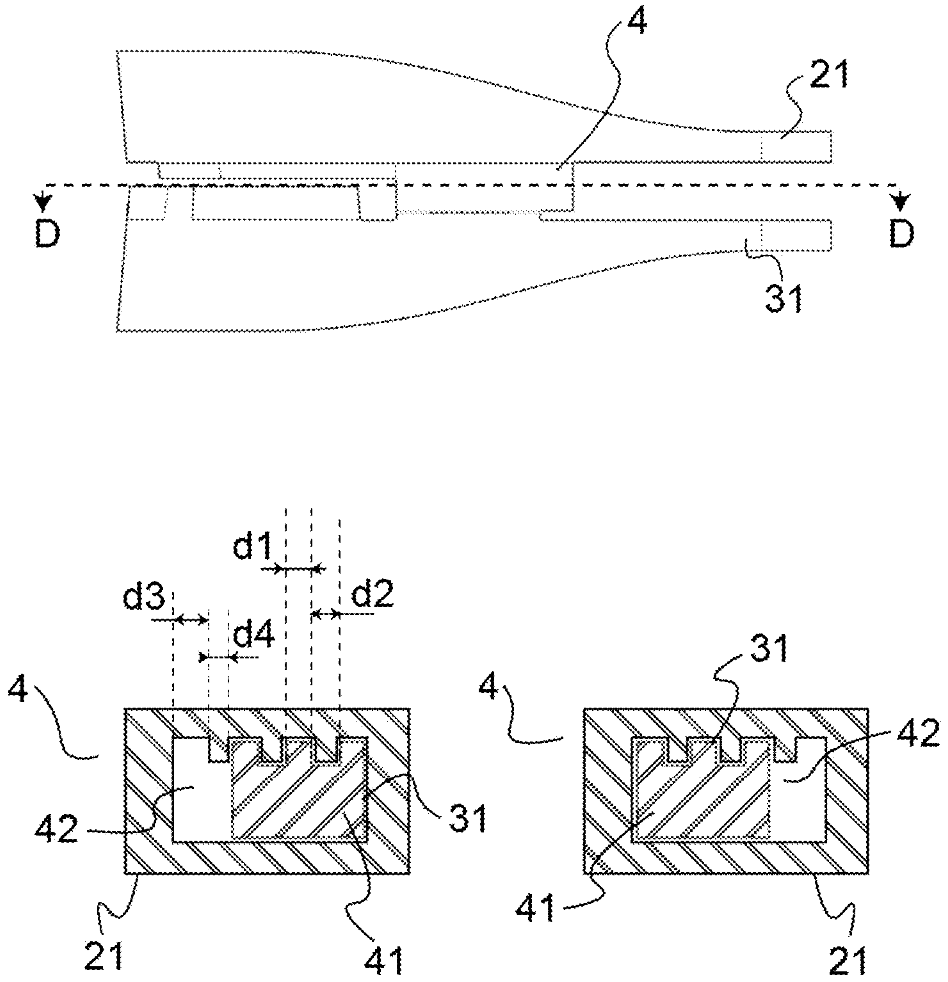
FIG. 17 is a cross-sectional schematic diagram of the adjustment part in accordance with one embodiment.
Figure 18:
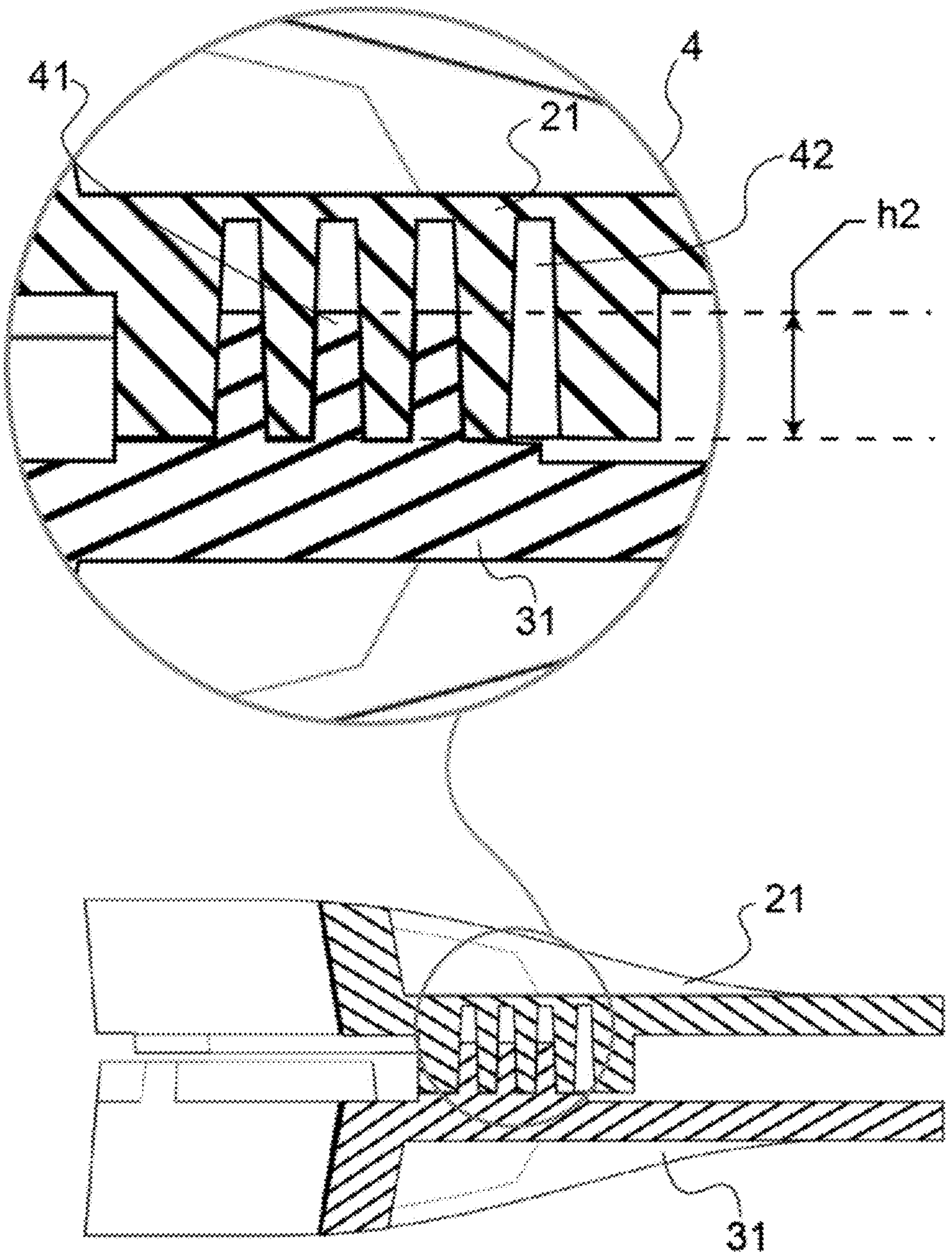
FIG. 18 is an enlarged cross-sectional schematic diagram of the adjustment part in accordance with one embodiment.

In other embodiments, the protrusion 41 and the protrusion receiving part 42 are made of metal or another material with a thin wall thickness capable of robust connection, and each adjustment position can be set to less than 2 mm, allowing for finer distance adjustment. For example, the protrusion 41 can have a shape of E, as depicted in FIG. 17. In one configuration, each E's protruding edge is 0.5 mm in length, labeled as d1 in FIG. 17, and each recessed edge also is 0.5 mm in length, labeled as d2 in FIG. 17. Each time an adjustment position is moved, the movement distance is 1 mm, which is the sum of d1 and d2. Similarly, the protrusion receiving part 42 corresponds to the protrusion 41 with an E-shaped groove. The length of each E's protruding edge is denoted as d3 in FIG. 17, and the length of the recessed edge is labeled as d4 in FIG. 17.

Additionally, the technical features described in the aforementioned embodiments can be combined as needed to create a mandibular advancement device 1 that includes all or part of these technical features.

The implementation of a mandibular advancement device with an adjustment part at least includes the following benefits:

1. Mandibular advancement devices typically require precise distance adjustment. Fine adjustment helps to avoid the risks associated with over-adjustment, which can lead to excessive advancement distance. This excessive distance can cause pain and discomfort in the jaw joint and inside the mouth, and may even lead to disorders of the temporomandibular joint, oral ulcers, and other soft tissue injuries. Furthermore, by finely adjusting and gradually increasing the advancement distance, users can more easily adapt to the device, making the wearing process more comfortable and thus improving compliance and willingness to wear. Additionally, the fine adjustment of the advancement distance facilitates a gradual adaptation to the treatment process, ultimately enhancing the therapeutic effectiveness of the device. Although other structures on the market offer fine adjustment, many issues still persist. For instance, while bolt adjustment allows for precise settings, the addition of small parts can lead to bolts loosening. If a bolt falls out, it may enter the esophagus or even the airway, posing significant potential hazards. Another design includes an external connecting arm; if made from rigid materials, it tends to scratch the edges of the mouth, whereas if made from flexible materials, it tends to loosen and fail to secure properly. Gear structures, similar to snap-fit configurations but different in assembly, typically require force to adjust the advancement distance back and forth. Gear structures also need to be made from more rigid materials to prevent loosening or wear, commonly using polycarbonate materials. However, mandibular advancement devices often require the heating of moldable components, and polycarbonate materials can release bisphenol A when heated, which poses health hazards. Moreover, the finer edges of gears make it difficult to align left and right, potentially leading to inconsistent advancement distances that can affect the treatment outcome. To address these issues, this disclosure employs specially designed snap-fit structures, such as I-shaped, F-shaped, E-shaped, and symmetric E-shaped configurations. The special snap-fit design not only ensures the required wall thickness during production but also maintains structural stability. Whether I-shaped, F-shaped, E-shaped, or symmetric E-shaped, these are integral structures secured by snapping together from top to bottom, thus facilitating easier operation during the assembly process. The snap-fit structure of this disclosure provides a more reliable and flexible solution, meeting the needs for precise adjustment of the mandibular advancement distance and ensuring the stability of the device's function, while also making it easier for users to operate and adjust.

2. The disclosure incorporates an integrated snap-fit structure, enabling multi-position adjustment on a single pair of upper and lower frames. This design allows users to adjust the forward movement of the lower tray assembly according to personal needs, selecting the most effective and comfortable position, thereby enhancing the compliance to the mandibular advancement device. Compared to using multiple different combinations of upper and lower frames, this disclosure utilizes specially designed snap-fit structures such as I-shaped, F-shaped, E-shaped, and symmetric E-shaped. A single pair of upper and lower frames can now provide more precise and varied forward adjustment positions. This design not only eliminates the need for multiple frames but also enables more position adjustments on a single frame while ensuring the precision of the adjustment range. This offers a more economical and simpler solution, reducing costs and operational complexity.

3. Existing mandibular advancement devices available on the market still have issues with slipping out during sleep, with many users reporting that the device often detaches from the teeth, leading to device fallout. Testing and analysis have shown that this detachment issue is primarily due to the necessary forward movement of the lower tray assembly relative to the upper tray assembly, combined with possible movements or involuntary mouth opening by the user during sleep, all of which can lead to the device slipping off. To address this issue, the upper and lower tray assemblies need to provide sufficient support in their forward and backward positioning to ensure the device remains securely in place during use. Moreover, each tooth has a certain angular difference and is not necessarily perpendicular to the horizontal plane. For example, the anterior teeth (central and lateral incisors) are usually inclined towards the lip at an angle of about 10° to 25° from the vertical plane; canines (towards the lip side) have an inclination of about 5° to 15°; and molars (towards the lip side) usually have an inclination of 0 to 5°. The anterior teeth and canines have a larger angle relative to the vertical plane, whereas molars have a smaller angle, leading to different support needs when the user bites down. Existing mandibular advancement devices often have frames with inner and outer walls set perpendicular to the bottom walls, a design that does not accommodate the natural shape of the teeth, leading to discomfort and ease of slippage when worn. Another common design of frames of mandibular advancement devices consists only of bottom walls without setting inner and outer walls in the forward and backward position, lacking sufficient support and allowing teeth to easily slide out of the device. After multiple tests with users of various tooth forms, this disclosure provides an improved frame design. The frame provided by this disclosure has inner and outer walls to provide adequate support. Moreover, an angle is formed between the inner walls and the bottom walls to accommodate the natural inclination of the anterior teeth towards the lip, thereby fitting more closely to the shape of the teeth. Through this structural design, the mandibular advancement device provided by this disclosure has shown significant stability in experimental trials, reducing the likelihood of the device falling out. This design also enhances comfort and effectiveness when worn, addressing major issues with existing products.

The technical features of the above embodiments can be freely combined. For brevity, not all possible combinations of these features are described here. However, as long as the combinations do not introduce contradictions, they should be considered within the scope outlined by this disclosure.

The embodiments described above represent only a few of the possible implementations of the disclosure. Although the descriptions are specific and detailed, they should not be understood as limiting the scope of this disclosure. It should be noted that for one skilled in the art, various modifications and improvements can be made without departing from the concept of the disclosure, and these are also considered within the scope of protection of this disclosure. Therefore, the scope of protection for this disclosure should be determined by the appended claims.

It must be noted that as used herein and in the appended claims, the singular forms "a", "an", and "the" include their plural equivalents, unless the context clearly dictates otherwise.

The invention claimed is:

1. A mandibular advancement device, comprising:

an upper tray assembly, arch-shaped and configured to conform to a curvature of an upper dental arch of a user;

a lower tray assembly spaced from the upper tray assembly is a first direction, arch-shaped and configured to conform to a curvature of a lower dental arch of the user;

wherein the upper tray assembly comprises an upper frame and an upper moldable component;

wherein the lower tray assembly comprises a lower frame and a lower moldable component;

wherein the upper tray assembly and/or the lower tray assembly includes at least two different materials; and an adjustment part configured to connect the upper tray assembly and the lower tray assembly by a snap-fit, and to adjust a position of the lower tray assembly relative to the upper tray assembly;

wherein the snap-fit includes at least one protrusion and at least one protrusion receiving part on one side of the upper tray assembly and the lower tray assembly, wherein the at least one protrusion is configured to compressively connect the upper frame and the lower frame, wherein each of the at least one protrusion and the at least one protrusion receiving part has a length in a second direction and a width in a third direction, wherein the length of the at least one protrusion is less than the length of the at least one protrusion receiving part, and wherein each of the at least one protrusion and the at least one protrusion receiving part have two sidewalls extending in the second direction, the two sidewalls having interlocking nonplanar surfaces to prevent movement of the at least one protrusion in the second direction.

2. The mandibular advancement device according to claim 1, wherein the upper tray assembly is configured to contact the upper dental arch of the user.

3. The mandibular advancement device according to claim 1, wherein the lower tray assembly is configured to contact the lower dental arch of the user.

4. The mandibular advancement device according to claim 1, wherein the upper moldable component is configured to soften upon heating to allow it to be adjusted and molded into a shape to match the upper dental arch when the user bites down.

5. The mandibular advancement device according to claim 1, wherein the lower moldable component is configured to soften upon heating to allow it to be adjusted and molded into a shape to match the lower dental arch when the user bites down.

6. A mandibular advancement device, comprising:

an upper tray assembly comprising an upper frame and an upper moldable component;

a lower tray assembly comprising a lower frame and a lower moldable component;

wherein the upper tray assembly and/or the lower tray assembly includes at least two different materials; and an adjustment part configured to connect the upper tray assembly and the lower tray assembly by a snap-fit, and to adjust a position of the lower tray assembly relative to the upper tray assembly between a first predetermined position and a second predetermined position;

wherein the snap-fit includes at least one protrusion and at least one protrusion receiving part on one side of the upper tray assembly and the lower tray assembly, and the at least one protrusion receiving part comprises two sidewalls and two end walls, wherein the at least one protrusion is configured to compressively connect the upper frame and the lower frame;

wherein the upper frame and the lower frame each have at least one inner wall and at least one outer wall, wherein the at least one protrusion has a first position in the at least one protrusion receiving part when the lower tray assembly is in the first position relative to the upper tray assembly, wherein the at least one protrusion has a second position in the at least one protrusion receiving part when the lower tray assembly is in the second position relative to the upper tray assembly, wherein a sidewall of the at least one protrusion has at least one protruding edge and a sidewall of the at least one protrusion receiving part has at least one recessed edge, and wherein the at least one protruding edge and the at least one recessed edge retain the at least one protrusion in the first position or the second position.

7. The mandibular advancement device according to claim 6, wherein the upper frame and the lower frame each have at least one bottom wall, the at least one protrusion is provided on a surface of the at least one bottom wall of the upper frame, and the at least one protrusion receiving part is provided on a surface of the at least one bottom wall of the lower frame, and is opposite the at least one protrusion.

8. The mandibular advancement device according to claim 6, wherein the upper frame and the lower frame each have at least one bottom wall, the at least one protrusion is provided on the surface of the at least one bottom wall of the lower frame, and the at least one protrusion receiving part is provided on the surface of the at least one bottom wall of the upper frame, and is opposite the at least one protrusion.

9. The mandibular advancement device according to claim 6, wherein the upper moldable component and the lower moldable component include a flexible thermoplastic material.

10. The mandibular advancement device according to claim 6, wherein the upper frame and the lower frame include a relatively rigid material compared to the upper moldable component and lower moldable component.

11. A mandibular advancement device, comprising:

an upper tray assembly comprising an upper frame and an upper moldable component;

a lower tray assembly comprising a lower frame and a lower moldable component;

wherein the upper tray assembly and/or the lower tray assembly includes at least two different materials and the lower tray assembly is spaced from the upper tray assembly in a first direction; and an adjustment part configured to connect the upper tray assembly and the lower tray assembly by a snap-fit, and to adjust a position of the lower tray assembly relative to the upper tray assembly;

wherein the upper frame and the lower frame each have at least one inner wall, wherein the adjustment part includes at least one protrusion and at least one protrusion receiving part on one side of the upper tray assembly and the lower tray assembly, wherein the at least one protrusion has a first position in the at least one protrusion receiving part when the lower tray assembly is in the first position relative to the upper tray assembly, wherein the at least one protrusion has a second position in the at least one protrusion receiving part when the lower tray assembly is in the second position relative to the upper tray assembly, wherein the at least one protrusion and the at least one protrusion receiving part retain the at least one protrusion in the first position or the second position, wherein each of the at least one protrusion and the at least one protrusion receiving part has a length in a second direction and a width in a third direction, wherein the length of the at least one protrusion is less than the length of the at least one protrusion receiving part, and wherein each of the at least one protrusion and the at least one protrusion receiving part have two sidewalls extending in the second direction, the two sidewalls having interlocking nonplanar surfaces to prevent movement of the at least one protrusion in the second direction.

12. The mandibular advancement device according to claim 11, wherein a total weight of the upper frame and the lower frame is between 3 g to 50 g.

13. The mandibular advancement device according to claim 11, wherein a total weight of the mandibular advancement device is between 8 g to 80 g.

14. The mandibular advancement device according to claim 11, wherein the snap-fit of the adjustment part is configured in one of the following shapes: I-shaped, F-shaped, E-shaped, or symmetrically E-shaped.

15. The mandibular advancement device according to claim 11, wherein the adjustment part is configured to adjust multiple positions.

16. A mandibular advancement device, comprising:

an upper tray assembly comprising an upper frame and an upper moldable component;

a lower tray assembly comprising a lower frame and a lower moldable component;

wherein the lower tray assembly spaced from the upper tray assembly is a first direction wherein the upper tray assembly and/or the lower tray assembly includes at least two different materials; and an adjustment part configured to connect the upper tray assembly and the lower tray assembly by a snap-fit, and to adjust a position of the lower tray assembly relative to the upper tray assembly;

wherein the upper frame and the lower frame each have a left side, a right side, at least one inner wall, at least one outer wall, and at least one bottom wall; and wherein a vertical distance between the at least one inner wall, the at least one outer wall, and the at least one bottom wall between 0.5 mm to 20 mm;

wherein the adjustment part includes at least one protrusion and at least one protrusion receiving part on one side of the upper tray assembly and the lower tray assembly, the at least one protrusion receiving part is configured to be a centrally symmetric structure, wherein the at least one protrusion has a first predetermined position in the at least one protrusion receiving part when the lower tray assembly is in the first position relative to the upper tray assembly, wherein the at least one protrusion has a second predetermined position in the at least one protrusion receiving part when the lower tray assembly is in the second position relative to the upper tray assembly, wherein the at least one protrusion and the at least one protrusion receiving part retain the at least one protrusion in the first position or the second position, wherein each of the at least one protrusion and the at least one protrusion receiving part has a length in a second direction and a width in a third direction, wherein the length of the at least one protrusion is less than the length of the at least one protrusion receiving part, and wherein the at least one protrusion and the at least one protrusion receiving part prevent movement of the at least one protrusion in the second direction.

17. The mandibular advancement device according to claim 16, wherein a thickness of the at least one bottom wall of the upper frame and the lower frame is between 0.5 mm to 20 mm.

18. The mandibular advancement device according to claim 16, wherein the upper tray assembly and/or the lower tray assembly includes at least one channel pillar, and when the upper tray assembly is combined with the lower tray assembly, gaps between the upper tray assembly and the lower tray assembly and the at least one channel pillar jointly form at least one airflow channel.

19. The mandibular advancement device according to claim 18, wherein a number of the at least one channel pillar is odd.

20. The mandibular advancement device according to claim 18, wherein a number of the at least one airflow channel is even and a structure of the at least one airflow channel is symmetrical.

* * * * *